United States Patent
Turner et al.

(10) Patent No.: US 8,857,262 B2
(45) Date of Patent: Oct. 14, 2014

(54) SYSTEMS AND METHODS FOR ULTRASONICALLY EVALUATING STRUCTURAL PROPERTIES

(75) Inventors: Joseph A. Turner, Lincoln, NE (US); Christopher M. Kube, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 314 days.

(21) Appl. No.: 13/305,888

(22) Filed: Nov. 29, 2011

(65) Prior Publication Data

US 2012/0132005 A1     May 31, 2012

Related U.S. Application Data

(60) Provisional application No. 61/417,485, filed on Nov. 29, 2010.

(51) Int. Cl.
*G01N 29/04* (2006.01)
*G01N 29/50* (2006.01)
*B61K 9/10* (2006.01)
*G01N 29/06* (2006.01)
*G01N 29/44* (2006.01)

(52) U.S. Cl.
CPC .......... *G01N 29/50* (2013.01); *G01N 2291/044* (2013.01); *G01N 2291/2632* (2013.01); *G01N 2291/2634* (2013.01); *G01N 2291/0289* (2013.01); *B61K 9/10* (2013.01); *G01N 29/043* (2013.01); *G01N 2291/105* (2013.01); *G01N 29/069* (2013.01); *G01N 2291/0258* (2013.01); *G01N 29/4472* (2013.01)
USPC .............................................. 73/597; 73/602

(58) Field of Classification Search
USPC ............................ 73/597, 602, 636, 639, 643
See application file for complete search history.

(56) References Cited

U.S. PATENT DOCUMENTS

| | | | |
|---|---|---|---|
| 4,010,636 A | 3/1977 | Clark et al. | |
| 3,060,005 A | 6/1978 | Vezina | |
| 4,283,953 A | 8/1981 | Plona | |
| 4,435,984 A | 3/1984 | Gruber | |
| 4,718,277 A * | 1/1988 | Glascock | ........................ 73/622 |

(Continued)

FOREIGN PATENT DOCUMENTS

| | | |
|---|---|---|
| EP | 2182351 A1 | 5/2010 |
| JP | 7174643 A | 7/1995 |
| RU | 1801844 A1 | 3/1993 |

OTHER PUBLICATIONS

Ghoshal, Goutam et al., "Diffuse Ultrasonic Backscatter in a Two-Dimensional Domain", ACTA Mechanica, vol. 205, No. 1-4, pp. 35-49, Apr. 21, 2009.

(Continued)

*Primary Examiner* — J M Saint Surin
(74) *Attorney, Agent, or Firm* — Davis, Brown, Koehn, Shors & Roberts, P.C.; Sean D. Solberg

(57) ABSTRACT

Systems and methods for ultrasonically evaluating one or more microstructural material properties of a structural specimen are disclosed. An example system comprises an ultrasonic sensor unit including a plurality of ultrasonic transducers that generate ultrasonic backscatter within the specimen, and an evaluation module that performs an autocorrelation function on the ultrasonic backscatter data. An autocorrelation algorithm is configured to execute a single scattering response (SSR) model that computes second order grain statistics of the structural specimen.

22 Claims, 9 Drawing Sheets

(56) References Cited

U.S. PATENT DOCUMENTS

| | | | |
|---|---|---|---|
| 4,995,320 A * | 2/1991 | Sato et al. | 104/118 |
| 5,020,371 A | 6/1991 | Panetti | |
| 5,335,184 A | 8/1994 | Hildebrand | |
| 5,341,683 A | 8/1994 | Searle | |
| 5,386,727 A | 2/1995 | Searle | |
| 5,390,544 A | 2/1995 | Madras | |
| 5,721,685 A | 2/1998 | Holland et al. | |
| 5,753,808 A | 5/1998 | Johnson | |
| 6,044,698 A | 4/2000 | Bryan | |
| 6,119,353 A | 9/2000 | Gr.o slashed.nskov | |
| 6,430,875 B1 | 8/2002 | Clark et al. | |
| 6,647,891 B2 | 11/2003 | Holmes et al. | |
| 6,742,392 B2 | 6/2004 | Gilmore et al. | |
| 7,231,826 B2 * | 6/2007 | Bossi et al. | 73/618 |
| 7,403,296 B2 | 7/2008 | Farritor et al. | |
| 7,484,413 B2 * | 2/2009 | Georgeson et al. | 73/624 |
| 7,755,774 B2 | 7/2010 | Farritor et al. | |
| 7,920,984 B2 | 4/2011 | Farritor | |
| 7,937,246 B2 | 5/2011 | Farritor et al. | |
| 7,942,058 B2 | 5/2011 | Turner | |
| 8,418,562 B2 * | 4/2013 | Clossen-Von Lanken Schulz et al. | 73/632 |
| 2004/0003662 A1 | 1/2004 | Kenderian et al. | |
| 2005/0072236 A1 | 4/2005 | Heyman et al. | |
| 2006/0136152 A1 | 6/2006 | Takahashi | |
| 2007/0214892 A1 | 9/2007 | Turner et al. | |
| 2009/0056454 A1 | 3/2009 | Turner | |
| 2010/0288049 A1 | 11/2010 | Hoyt | |
| 2011/0098942 A1 | 4/2011 | Turner | |
| 2011/0166827 A1 | 7/2011 | Farritor et al. | |

OTHER PUBLICATIONS

International Search Report and Written Opinion issued in PCT/US2011/062383, mailed Mar. 5, 2012, 11 pages.

Lu, S. et al. "Measurement of Vertical Track Modulus From a Moving Railcar," Proceedings of the AREMA 2006 Annual Conference, Louisville, KY, Sep. 17, 2006.

Lu, S. et al., "On the Relationship Between Load and Deflection in Railroad Track Structure," Proceedings of the AREMA 2008 Annual Conference, Salt Lake City, UT, Sep. 21, 2008.

Lu, Sheng et al., "Exception Criteria in Vertical Track Deflection and Modulus", 2007 ASME/IEEE Joint Rail Conference & Internal Combustion Engine Spring Technical Conference, Mar. 13, 2007, Pueblo, CO USA, 12 pages.

* cited by examiner

SYSTEMS AND METHODS FOR ULTRASONICALLY EVALUATING STRUCTURAL PROPERTIES

CROSS-REFERENCE TO RELATED APPLICATION

This application claims priority to U.S. Provisional Application No. 61/417,485, entitled "Stress Determination In Heterogeneous Materials," filed Nov. 29, 2010, the contents of which are incorporated herein by reference in their entirety for all purposes.

FEDERALLY SPONSORED RESEARCH OR DEVELOPMENT

This invention was made with government support under FRA grant DTFR53-04-G-00011. The government has certain rights in the invention.

TECHNICAL FIELD

The present disclosure relates generally to non-destructive techniques for analyzing materials. More specifically, the present disclosure pertains to ultrasonic systems and methods for determining and monitoring changes in microstructural material properties.

BACKGROUND

Structural health monitoring is used in many different industries for analyzing stress and other material characteristics of structures. Stress field measurement techniques can be used, for example, for analyzing railroad wheels and tracks, civil structures such as dams and bridges, and other applications that require continual stress monitoring over the life of the structure. Monitoring stress in these structures is important for a variety of reasons, including the performance of accurate preventative maintenance before degradation or failure of the structure.

Destructive techniques are sometimes utilized for performing stress monitoring of structures. One such method utilizes strain gauges which are nondestructive in the sense that they must be affixed to a structure. Strain gauges measure the strain at a point on a structure that can be associated with the structure's stress field. Due to their permanent attachment at discrete localized positions, however, strain gauges are often insufficient for gathering stress information representative of the entire structure. In addition, the permanent placement of strain gauges on structures is often laborious and costly when dealing with calibration and general maintenance. In the monitoring of stresses in structures such as railroad rails, for example, the use of strain gauges is often cost prohibitive due to the excessive number of gauges necessary to acquire an accurate understanding of the variation of stresses and strains that may exist along the length of a rail.

Nondestructive evaluation methods such as X-ray and neutron diffraction techniques are capable of monitoring localized changes in strain and for measuring stress fields, but are often impractical due to their high cost and portability constraints. Nondestructive evaluation methods such as ultrasonic techniques have also been developed and are used in an effort to supplant the inadequacies of strain gauges and to provide portable systems at lower costs compared to diffraction techniques. In particular, ultrasonic evaluation techniques based on the theory of acoustoelasticity have been used to monitor stresses in loaded structures. Acoustoelasticity describes the change in velocity of elastic wave propagation in a material under an applied stress. Ultrasonic techniques based on the theory of acoustoelasticity have been employed to relate applied stresses to the change in velocity of elastic waves. These relative changes in wavespeed can also be related to strains occurring in the structure.

The practical applicability of ultrasonic evaluation methods based on wavespeed calculations is somewhat limited. To perform these calculations, a pitch-catch configuration of ultrasonic transducers comprising source and receiver transducers separated by a specified distance is commonly used. The amount of time needed for a wave to traverse this distance is directly proportional to the wavespeed and is related to the material's stress state through the acoustoelastic theory. Generally, the separation distance needs to be large enough to allow for sufficient resolution of the received signals. Furthermore, the surface geometry of the structure being analyzed needs to be uniform to prevent edge reflection effects. As a result, these factors place constraints on the shape and dimensions of the structure that can be measured. Another issue is the limited resolution observed over practical ranges of stresses. This limitation can present measurement and calibration issues when correcting for temperature gradients and elongation effects within the structure.

SUMMARY

The present disclosure relates to ultrasonic systems and methods for determining and monitoring changes in microstructural material properties. An example system comprises an ultrasonic sensor unit including a plurality of ultrasonic transducers configured for operating in a pulse-echo mode for transmitting ultrasonic waves to a target region on or within a structural specimen and receiving ultrasonic backscatter signals responsive to the ultrasonic waves; and an evaluation module configured for receiving the ultrasonic backscatter signals, the evaluation module configured for performing a statistical autocorrelation function on the ultrasonic backscatter signals and determining one or more microstructural material properties of the specimen.

A system for ultrasonically evaluating one or more microstructural properties of a railroad rail comprises an ultrasonic sensor unit including a plurality of ultrasonic transducers configured for operating in a pulse-echo mode for transmitting ultrasonic waves to a target region on or within a railroad rail and receiving ultrasonic backscatter signals responsive to the ultrasonic waves, the plurality of ultrasonic transducers comprising a normal incidence ultrasonic transducer configured for inducing longitudinal mode wave ultrasonic waves within the rail and at least one oblique incidence ultrasonic transducer configured for inducing shear wave mode ultrasonic waves within the rail; and an evaluation module configured for receiving the ultrasonic backscatter signals, the evaluation module configured to execute an autocorrelation algorithm for performing a statistical autocorrelation function on the ultrasonic backscatter signals and determining one or more microstructural material properties of the railroad rail.

An example method for ultrasonically determining one or more microstructural material properties of a structural specimen comprises transmitting a plurality of pulsed ultrasonic waves to a single point on a structural specimen; sensing ultrasonic backscatter signals responsive to the pulsed ultrasonic waves; selecting a time window for analyzing the ultrasonic backscatter signals; performing an autocorrelation function on the time-windowed ultrasonic backscatter signals; and determining one or more microstructural material properties of the structural specimen.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
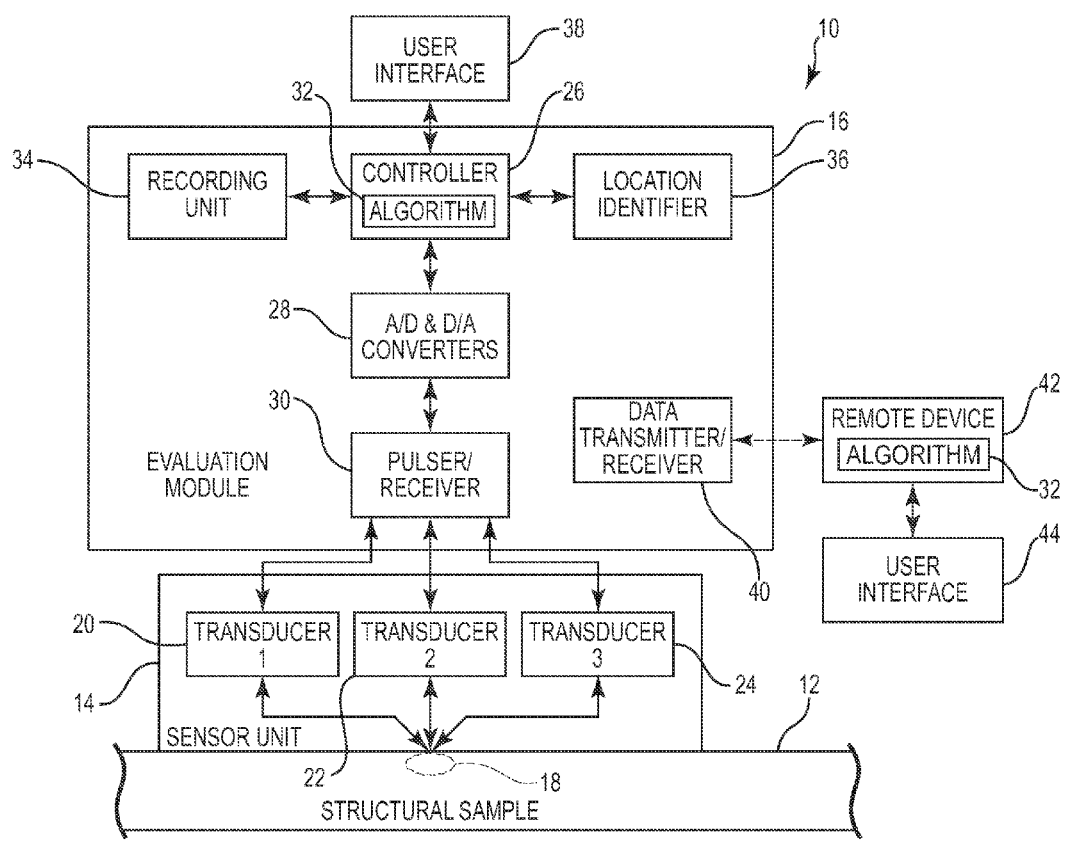
FIG. 1 is a block diagram of an example system for ultrasonically analyzing the microstructural properties of a structural sample.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a block diagram of an example system 10 for ultrasonically analyzing the microstructural properties of a structural sample 12. As shown in FIG. 1, the system 10 includes an ultrasonic sensor unit 14 and an evaluation module 16, which can be used to analyze localized stresses at one or more target locations 18 on or within the structural sample 12 by analyzing ultrasonic backscattering effects of ultrasonic waves transmitted into the sample 12. In certain embodiments, for example, the system 10 can be used for determining microstructural material properties such as stresses and strains within a railroad rail sample 12 by analyzing the ultrasonic backscattering properties of multiple ultrasonic waves transmitted from the ultrasonic sensor unit 14 to a target location 18 on or within the sample 12. The system 10 can also be used for analyzing other types of structures such as dams, bridges, buildings, storage tanks, and pressure vessels.

The ultrasonic sensor unit 14 includes a plurality of ultrasonic transducers 20, 22, 24 each configured to operate in a pulse-echo mode for transmitting pulsed ultrasonic waves into the structural sample 12. The resulting ultrasonic backscatter by the transmission into and reflection of these ultrasonic waves from the structural sample 12 is then sensed by the ultrasonic transducers 20, 22, 24 operating in a receive mode. In some embodiments, and as discussed further herein with respect to FIG. 3, the ultrasonic sensor unit 14 comprises two ultrasonic transducers 20, 22 configured for transmitting incident ultrasonic waves at an oblique angle relative to a surface of the structural sample 12 and a third ultrasonic transducer 24 configured for transmitting ultrasonic waves perpendicular to the surface of the structural sample 12. The number and configuration of the ultrasonic transducers 20, 22, 24 can vary in other embodiments. For example, additional ultrasonic transducers can be used for generating and transmitting oblique and normal incident ultrasonic waves into the sample 12. Furthermore, and in some embodiments, individual ultrasonic transducers are configured to operate independently in either transmitting or receiving modes. In some embodiments, an acoustic coupling medium such as water or oil or a solid couplant can be placed within the sensor unit casing to aid in acoustically coupling the ultrasonic transducers 20, 22, 24 to the structural sample 12. In some embodiments, the ultrasonic sensor unit 14 is stationary. In other embodiments, the ultrasonic sensor unit 14 is configured to move along the surface of the sample 12. In the evaluation of railroad rail, for example, the ultrasonic sensor unit 14 can be either statically coupled to the rail or configured to move along a surface of the rail such as the rail head or web.

The evaluation unit 16 is configured for evaluating the ultrasonic backscatter signals received by each of the ultrasonic transducers 20, 22, 24 operating in the receive mode. In some embodiments, the evaluation unit 16 comprises a controller 26, an analog-to-digital (A/D) and digital-to-analog (D/A) converter 28, and a pulser/receiver 30. Based on control signals from the controller 26, the pulser/receiver 30 provides electrical signals to the ultrasonic transducers 20, 22, 24 for generating pulsed ultrasonic waves in a transmission mode. The resulting ultrasonic backscatter waves received on the ultrasonic transducers 20, 22, 24 are then processed by the pulser/receiver 30, digitized, and fed back to the controller 26 for analysis by an autocorrelation algorithm 32 to determine one or more microstructural properties of the structural sample 12.

The ultrasonic backscatter data acquired from each of the ultrasonic transducers 20, 22, 24 can be stored in a recording unit 34 and/or can be relayed to one or more other devices for further processing. In some embodiments, the recording unit 34 stores the raw data obtained from each of the ultrasonic transducers 20, 22, 24, the structural data computed by the autocorrelation algorithm 32, as well as the control and operating parameters used by the system to acquire the raw and computed data.

In some embodiments, the evaluation unit 16 further includes a location identifier 36 such as a Global Positioning System (GPS) device for acquiring global location data that can be associated with backscatter data measurements obtained by the ultrasonic sensor unit 14. In some embodiments, such positioning data can be used to track the location of the ultrasonic sensor unit 14 relative to the structural sample 12, allowing backscatter data measurements acquired over time to be associated with the corresponding locations on the sample 12. In the analysis of railroad rail, for example, the global location data from the location identifier 36 can be used to associate and trend backscatter data measurements obtained along specific locations of the rail. In some embodiments, the system 10 is configured to trend this data to generate a stress gradient field of the entire rail. In contrast to structural health monitoring techniques that employ strain gauges to obtain localized measurements at discrete locations along the rail, the system 10 can be used to analyze stresses and strains within the entire structure, thus providing a better understanding of the actual condition of the structure.

A user interface 38 is configured for permitting users to view and analyze raw and processed data obtained via the ultrasonic sensor unit 14, to program the evaluation unit 16, and to perform other system functions. In certain embodiments, the user interface 38 comprises a graphical user interface (GUI) that can be used to view graphs, tables, or other visual data associated with a structure or multiple structures, either in real-time or based on data stored within the recording unit 34. In some embodiments, a data transmitter/receiver 40 is configured for wirelessly relaying data, settings, and other information back and forth between the evaluation unit 16 and a remote device 42 equipped with a remote user interface. As with user interface 38, the remote user interface 44 can also be used to view raw and processed data obtained via the ultrasonic sensor unit 14, to program the evaluation unit 16, and for performing other system functions. In some embodiments, the remote device 42 can be further configured to run an autocorrelation algorithm 32 to determine one or more characteristics (e.g., stress, strain, etc.) of the structural sample 12.

One or more components of the evaluation unit 16 and/or remote device 42 can be implemented in software, hardware, or a combination of both. In some embodiments, the systems and methods described herein can be executed as computer readable instructions on a programmable computer or processor comprising a data storage system with volatile and/or non-volatile memory.

Figure 2:
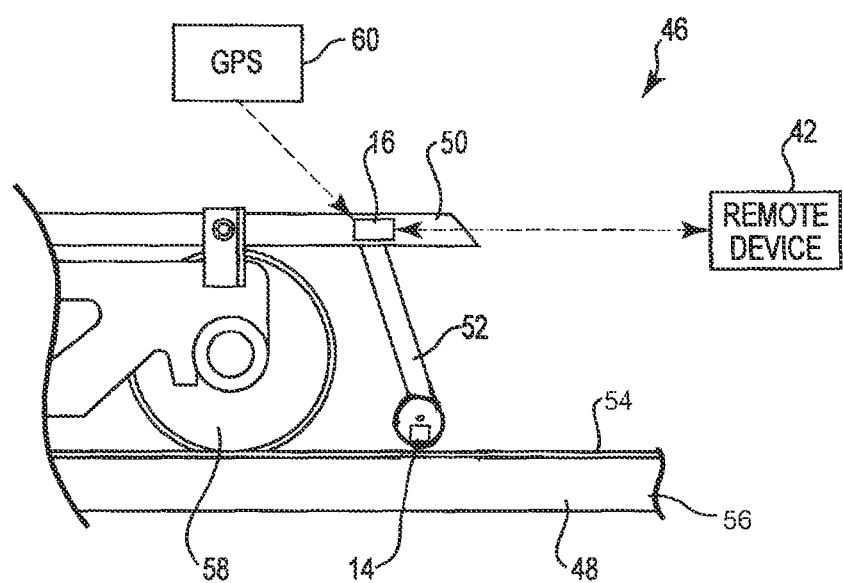
FIG. 2 is a schematic view of an example system for ultrasonically analyzing the microstructural properties of a railroad rail.

FIG. 2 is a schematic view of an example system 46 for ultrasonically analyzing the microstructural properties of a railroad rail 48. FIG. 2 may represent, for example, an implementation of the system 10 of FIG. 1 for measuring temperature-induced longitudinal stresses in a sample of continuous welded rail (CWR). In the embodiment of FIG. 2, the ultrasonic sensor unit 14 is coupled to a railcar 40 via a boom and rotating wheel assembly 52, and is configured to transmit ultrasonic waves into a portion of the rail 48 such as the head 54 or web 56. In other embodiments, the ultrasonic sensor unit 14 can be coupled to other locations on the railcar 50, including one of the wheels 58. In some embodiments, multiple ultrasonic sensor units 14 can be coupled to the railcar 50, and can be configured to sense different locations along the same rail 48 or along both rails 48. In some embodiments, for example, a first ultrasonic sensor unit 14 is tasked to obtain ultrasonic backscatter measurements along a first rail and a second ultrasonic sensor unit 14 is tasked to obtain ultrasonic backscatter measurements along the other rail. Multiple ultrasonic sensor units 14 can be employed to measure different locations along the same rail, such as the rail web and head. Other configurations are also possible.

During movement of the railcar 50 along the rail, the ultrasonic sensor unit 14 transmits ultrasonic waves into the rail 48 and senses the resultant backscatter waves. This data is then fed to the evaluation unit 16 for analysis. Location data obtained via a GPS system 60 is also received by the evaluation unit 16 and stored along with the backscatter measurements in the recording unit 34. In some embodiments, the raw backscatter data and location data are transmitted wirelessly to a remote device 42, which process the data to determine one or more microstructural properties associated with the rail 48. In other embodiments, the evaluation unit 16 computes one or more microstructural properties associated with the rail 48 and transmits this data to the remote device 42 either in real-time or at a later time for further analysis. In certain embodiments, the evaluation unit 16 is configured to store the raw and processed data in the recording unit 34 and transmit this data to the remote device 42 at periodic intervals and/or upon demand.

Figure 3:
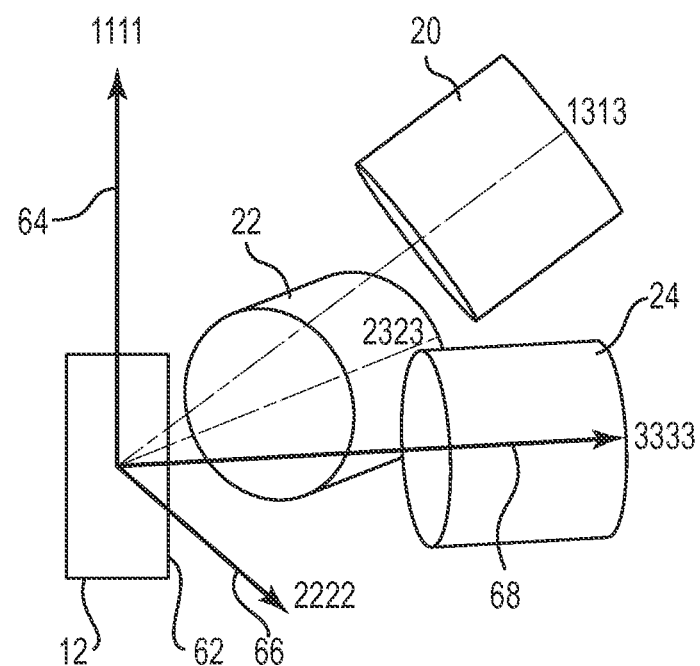
FIG. 3 is a schematic view of an example geometrical ultrasonic transducer configuration for generating longitudinal and oblique ultrasonic backscatter in a structural sample.

FIG. 3 is a schematic view of an example geometrical ultrasonic transducer configuration for generating longitudinal and oblique ultrasonic backscatter in a structural sample. FIG. 3 may represent, for example, an example spatial configuration of the ultrasonic transducers 20, 22, 24 used by the ultrasonic sensor unit 14 of FIG. 1. In the embodiment of FIG. 3, two ultrasonic transducers 20, 22 are oriented at different, oblique angles relative to the incident surface 62 of the structural sample 12, and are configured to generate shear wave mode backscatter in the directions indicated generally by arrows 64 and 66, respectively. A third ultrasonic transducer 24, in turn, is oriented normal to the incident surface 62, and is configured to generate longitudinal wave backscatter in the direction indicated generally by arrow 68.

In polycrystalline materials such as railroad rail, ultrasonic backscatter typically results from the multitude of reflections and refractions that occur at the grain boundaries due to variations of the single-crystal elastic moduli. The grain boundary is a single-phase interface in which the crystals on each side of the boundary are nearly identical except in their orientation. The scattering of ultrasound in polycrystalline materials is related to the applied stress through the covariance of the elastic moduli of the material. Both normal incidence (i.e., longitudinal) and oblique incidence (i.e., shear) measurements vary with applied stress, although at different degrees of variance based on a function containing several variables. For statistically isotropic distributions of grains, the covariance of moduli can be calculated in closed-form.

In some embodiments, a statistical approach based on diffuse ultrasonic backscatter can be used to obtain information about a material's microstructure, including the presence and location of cracks, voids, inclusions, or other properties that may compromise the strength and fatigue resistance of a structure. Statistical methods can also be used to extract the grain size in metals, where the grain diameter is within an order of magnitude of the ultrasonic wavelength. For a pulse-echo configuration such as that employed by the system 10 of FIG. 1, the evaluation unit 16 can be configured to perform a statistical analysis on the portion of the time domain response that corresponds to different locations within the bulk of the material. In some embodiments, the statistical model takes into consideration the transfer functions of the ultrasonic transducers 20, 22, 24 along with an appropriate time domain scattered response generated from the heterogeneous media to perform the analysis. If a material's spatial microstructural properties are known a priori, the stress field within the material can be deduced from the covariance of the elastic moduli.

Using a single scattering assumption, the backscattered response generated by the ultrasonic transducers 20, 22, 24 can be expressed as follows:

$$\Phi^1(t) = \Phi_{LL}^1(t) + \Phi_{TT}^1(t); \quad (1)$$

where $\Phi_{LL}^1(t)$ and $\Phi_{TT}^1(t)$ are the single scattering responses (SSR) due to the ultrasonic refraction at an arbitrary angle of incidence into the longitudinal and shear modes, respectively. The SSR for the longitudinal/shear mode can be expressed as:

$$\Phi^1_{LL/TT}(t) = \gamma_{LL/TT} \Xi_{LL/TT} \exp\left[-\frac{t^2}{\sigma^2}\right]; \quad (2)$$

where:

$\gamma_{LL/TT}$ represents experimental parameters related to the material and transducer;

$$\exp\left[-\frac{t^2}{\sigma^2}\right]$$

is a field distribution function related to the input pulse shape of the ultrasonic signal supplied to the ultrasonic transducer; and $\Xi_{LL/TT}$ is the stress-dependent elastic covariance tensor of the material.

Figure 4:
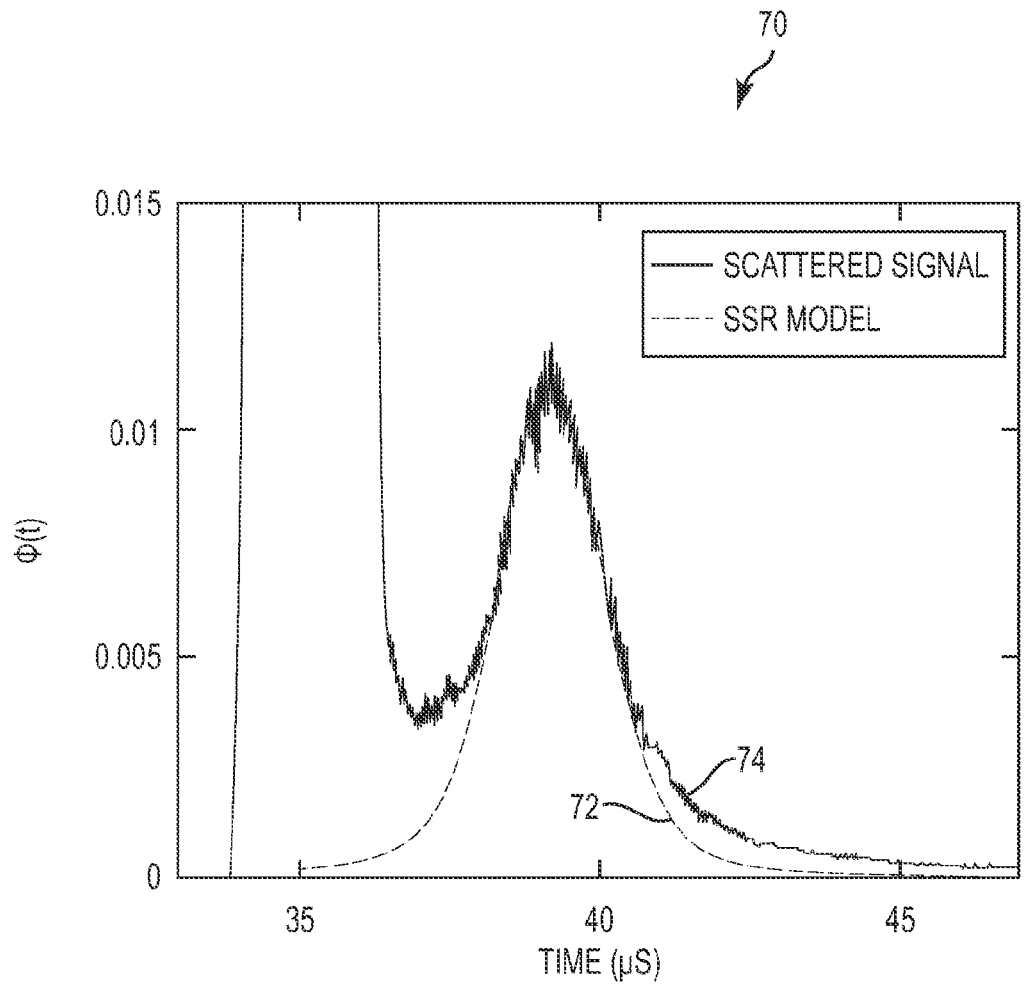
FIG. 4 is a graph showing example backscatter response data obtained using a single scattering response (SSR) model compared to experimental waveform data.

A graph 70 showing example backscatter response $\Phi(t)$ data 72 obtained from a single scattering response (SSR) model compared to experimental waveform data 74 obtained from a steel sample is shown in FIG. 4. For a normal incidence configuration in which shear wave energy is lower than the longitudinal modes by several order of magnitude, the SSR model data 72 closely approximates the experimental waveform data during the initial response period (i.e., at about 40 μs) and then deviates from the scattered signal during the latter portion of the response. This deviation can be contributed to higher order scattering effects as increasing times are impacted by multiple scattering.

The elastic covariance tensor in Equation (2) above can be represented by a quadratic equation with respect to a stress state that includes an applied stress (T):

$$\Xi_{LL/TT}(T) = K_0 + K_1 T + K_2 T^2; \quad (3)$$

where $K_0$, $K_1$, and $K_2$ are the known stress dependent coefficients.

In some embodiments, the residual stresses within the material can also be used as part of this stress state to generate measurements in addition to, or in lieu of, the applied stress (T) in Equation (3) above.

Experimentally, and in some embodiments, the single scattered response can be found by scanning the surface of a material and collecting signals from different points within the material. In such case, the single scattered response is equivalent to the spatial variance of the collected signals based on the following equation:

$$\Phi_{EXP}^1(t) = \text{var}[V(t)] = \langle V(t)^2 \rangle - \langle V(t) \rangle^2; \quad (4)$$

where V(t) is a matrix of signals acquired at different locations in a conventional ultrasonic C-Scan.

In the SSR model, the second term $\langle V(t) \rangle$ in Equation (4) above is assumed to be zero since a well-designed diffuse-field measurement will typically have zero mean. The magnitude of the fluctuations seen in the variance calculation is a function of the number of grains insonified over the cross-sectional area. Ideally, a large number of signals should be collected to minimize the resulting fluctuations. In many practical applications, however, a large scanning area is not always feasible due to material geometry and transducer coupling constraints.

In some embodiments, a statistical autocorrelation method that utilizes only a single point measurement can be employed to determine one or more microstructural material properties of the sample. The relationship between the single point autocorrelation and the spatial variance is evident through the Wiener-Khinchin theorem and numerical techniques, which provides:

$$\sqrt{\int_{t_0}^{t_0+\tau_{LL/TT}} \Lambda(t) dt} \approx \int_{t_0}^{t_0+\tau_{LL/TT}} \langle V(t)^2 \rangle dt; \quad (5)$$

where:

$\tau_{LL/TT}$ comprises a time window over the single scattering region of the normal or oblique incident signal; and $\Lambda(t)$ is the single point autocorrelation function.

The left-hand side of Equation (5) above is proportional to the elastic covariance tensor $\Xi_{LL/TT}$(T) in Equation (3), and thus can be substituted as follows to permit single point stress measurements of a material's stress field to be obtained using the system 10 of FIG. 1:

$$\sqrt{\int_{t_0}^{t_0+\tau} \Lambda_{LL,TT}(t) dt} \propto K_0 + K_1 T + K_2 T^2 \quad (6)$$

Figure 5:
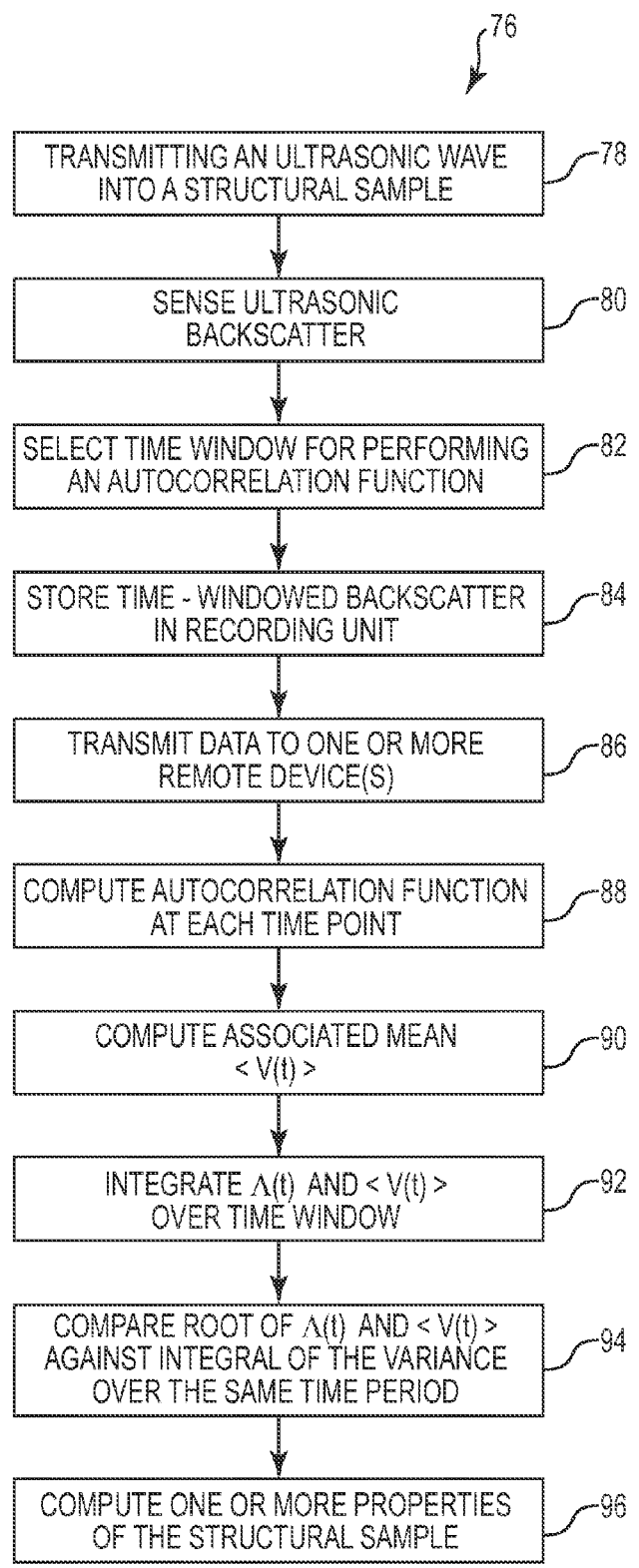
FIG. 5 is a block diagram of an example method for determining and monitoring changes in microstructural material properties using the system of FIG. 1.

FIG. 5 is a block diagram 76 of an example method for determining and monitoring changes in microstructural material properties using the system 10 of FIG. 1 and an autocorrelation function. The method 76 may begin generally at block 78 by transmitting an ultrasonic wave into a structural sample 12 to generate ultrasonic backscatter within the sample material. In some embodiments, for example, an ultrasonic sensor unit 14 including multiple ultrasonic transducers 20, 22, 24 each operating in a transmission mode can be used to generate longitudinal and shear waves within the specimen 12 to create measurable ultrasonic backscatter. In some embodiments, the ultrasonic transducers 20, 22, 24 are excited using a Gaussian modulated pulse generated from a pulser/receiver 30 such as the DPR500 available from Imaginant and JSR Ultrasonics of Pittsford, N.Y.

The ultrasonic backscatter data generated by the transmission of ultrasonic waves into the sample is sensed by the ultrasonic transducers 20, 22, 24 operating in a receive mode (block 80). A time window for performing an autocorrelation function is then selected (block 82) over a single scattering target region 18 for performing a statistical analysis on the backscatter data. Based on the time window, ultrasonic backscatter signals from each of the transducers 20, 22, 24 are gathered and stored as data in the recording unit 34 (block 84). In some embodiments, the backscatter data is also transmitted to one or more remote devices 42 for storage and/or further processing (block 86).

Using the time-windowed backscatter signal, the autocorrelation algorithm 32 performs an autocorrelation function of the time-windowed ultrasonic backscatter data. In some embodiments, the step of performing an autocorrelation function on the time-windowed data can be performed computationally using Equation (5) above, in which the autocorrelation function at each time point, and in some embodiments also their associated mean $\langle V(t) \rangle$, are calculated (blocks 88 and 90) and then integrated over a time window ($\tau$) (block 92). The root of these quantities are then compared to the integral of the variance $\int \langle V(t)^2 \rangle dt$, over the same time period (block 94).

Using the autocorrelated backscatter data, the system 10 can compute one or more microstructural material properties of the structural sample (block 96). In some embodiments, for example, the autocorrelated data can be used in conjunction with calibration data to compute the stress and/or strain at each target location on the structural sample as well as determine the location and presence of cracks, voids, inclusions, or other abnormalities. Other characteristics such as stress field gradients within the sample can also be determined using the autocorrelated data.

Figure 6:
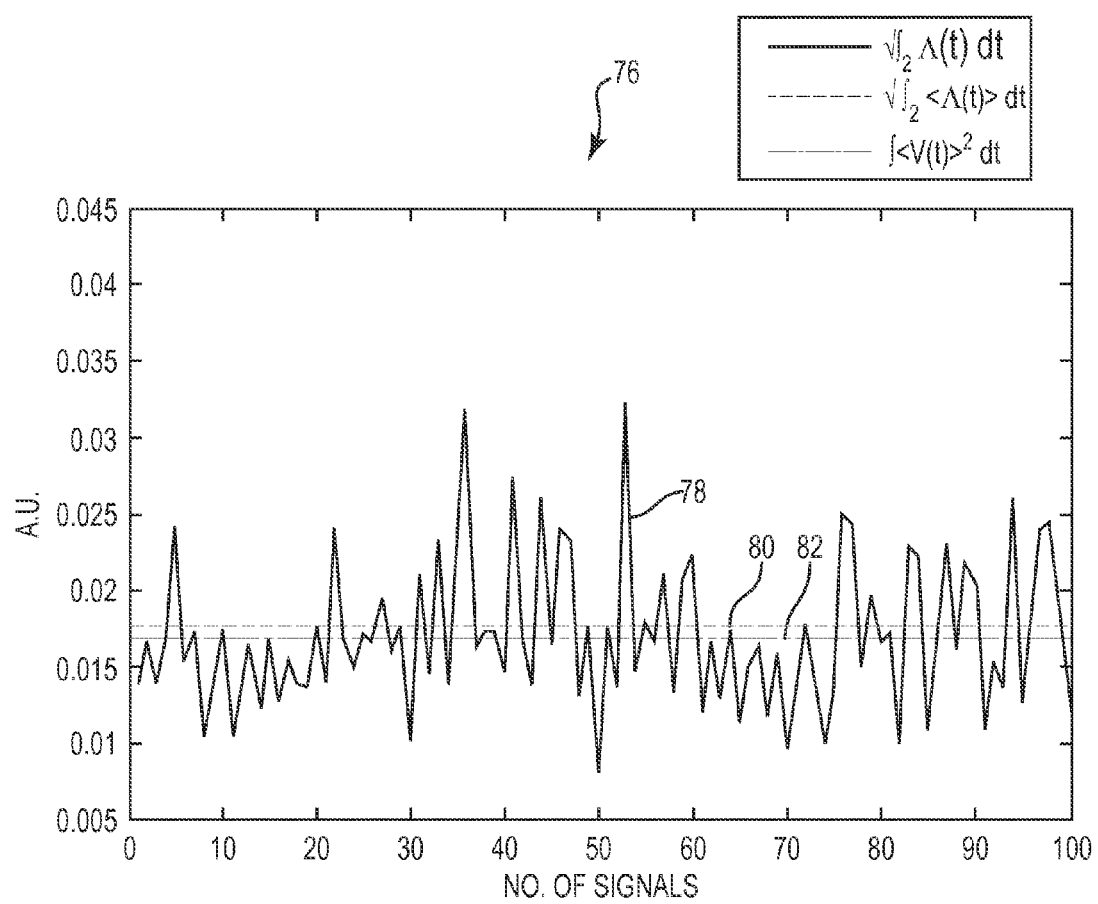
FIG. 6 is a graph showing autocorrelation functions for a sequence of ultrasonic scans.

An example implementation of the method 76 for use in analyzing aluminum and steel structural specimen will now be described. Using the system 10 of FIG. 1, a block of stress free steel was scanned using a 15 MHz focused, immersion type ultrasonic transducer having an aperture diameter of 0.5 in (1.27 cm) and a geometric focal length of about 3 inches (7.62 cm). In a normal incidence configuration, and as shown in the graph 76 of FIG. 6, one hundred scattered signals were collected and analyzed while maintaining a distance of 0.02 inches (0.05 cm) between any two consecutive scan locations to avoid recording correlated signals. The autocorrelation functions at each point, $\Lambda(t)$, and their mean, $<\Lambda(t)>$, were calculated and integrated over a time window ($\tau$), as shown by reference to lines 78 and 80, respectively. The root of these quantities were then compared to the integral of the variance, $\int <V(t)^2> dt$, over the same time window, as reflected by reference to line 82. The time integral of the mean autocorrelation differed by 4.46% to the integral of the variance. The single point autocorrelations had a standard deviation from the spatial variance equal to 0.49%. This deviation is much smaller than the expected change in magnitude of the single point autocorrelation during loading, thus validating the autocorrelation approach.

To investigate Equation (6) above, single point ultrasonic backscatter measurements were performed at normal and oblique incidence on samples of uniaxially loaded aluminum and steel rail samples in a direction indicated generally by arrow 64 in FIG. 3. The samples were loaded using a 453,000 lb (2015 kN) compressive press. The samples each had a cross-sectional area of 15.3 in$^2$ (98.7 cm$^2$), while the rail contained a cross-sectional area of 13.3 in$^2$ (85.9 cm$^2$). The maximum compression stresses generated on the samples were 204 MPa and 235 MPa, respectively.

Three focused ultrasonic transducers 20, 22, 24 operating in a pulse/echo configuration and having a geometric configuration such as that shown in FIG. 3 were utilized for measuring ultrasonic backscatter. Since the backscatter coefficients are dependent on the direction of incident ultrasound, different orientations of transducers will be more sensitive to the uniaxial load. Thus, the oblique incidence transducers 20, 22 were oriented at 18° from axis 3333 in FIG. 3 and generated shear wave modes ($\Phi_{TT}^1(t)$) propagating orthogonally to each other over the cross-section of the sample 12. The normal incidence ultrasonic transducer 24 generated a longitudinal wave mode ($\Phi_{LL}^1(t)$) perpendicular to the loading direction. The 18° angle of incidence was chosen to maximize the shear wave transmission while minimizing the longitudinal wave component in the steel sample. This angle of incidence also closely maximizes shear wave transmission and minimizes the longitudinal wave component in the aluminum sample. An angle of incidence of 19.5° can be used to maximize shear wave transmission and minimize longitudinal wave components in aluminum.

The ultrasonic transducers 20, 22, 24 can be mounted onto the sample 12 through a water-filled enclosure, which provides acoustic coupling between the transducer and the sample 12. The distance, or waterpath, between the ultrasonic transducers 20, 22, 24 and the sample 12 was chosen such that each transducer 20, 22, 24 would focus over the same grain volume. The waterpaths of 2.65 inches (6.73 cm) and 2.4 inches (6.11 cm) were used for the oblique ultrasonic transducers 20, 22 and normal incidence ultrasonic transducer 24, respectively. These waterpaths provided a focal depth of approximately 0.16 inches (0.4 cm) into the material.

A Gaussian modulated pulse generated from a pulser/receiver 30 was used for exciting the ultrasonic transducers 20, 22, 24. Since the scattering from the normal incidence ultrasonic transducer 24 is attenuated more than the oblique incidence ultrasonic transducers 20, 22, preamplified gains of 67 dB and 51 dB were used to compensate for signal strength. The resulting ultrasonic backscatter signals were acquired by a 12 bit analog-to-digital card at a sampling frequency of 500 MHz. A linear loading rate of 80,000 lb/min (36,287 kg/min) was used to load the samples from 0 to 453,000 lb (2015 kN). Using UTWIN™ ultrasonic C-scan software, the backscatter signals were collected using a proportional acquisition rate of 12 signals/min over the loading range. The collected backscatter signals from each ultrasonic transducer 20, 22, 24 were then post-processed and displayed. A graph 86 showing a sample waveform 88 generated for the normal incident transducer configuration is shown, for example, in FIG. 7A. A graph 90 showing a sample waveform 92 generated for the oblique incident transducer configurations is shown, for example, in FIG. 7B.

Figure 7A:
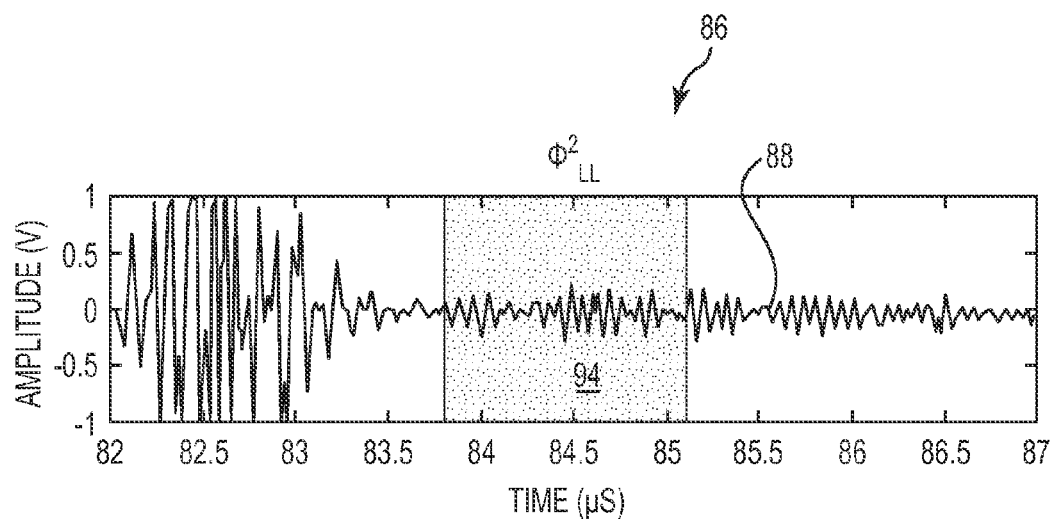
FIG. 7A is a graph showing a sample waveform generated for a normal incident ultrasonic transducer configuration.
Figure 7B:
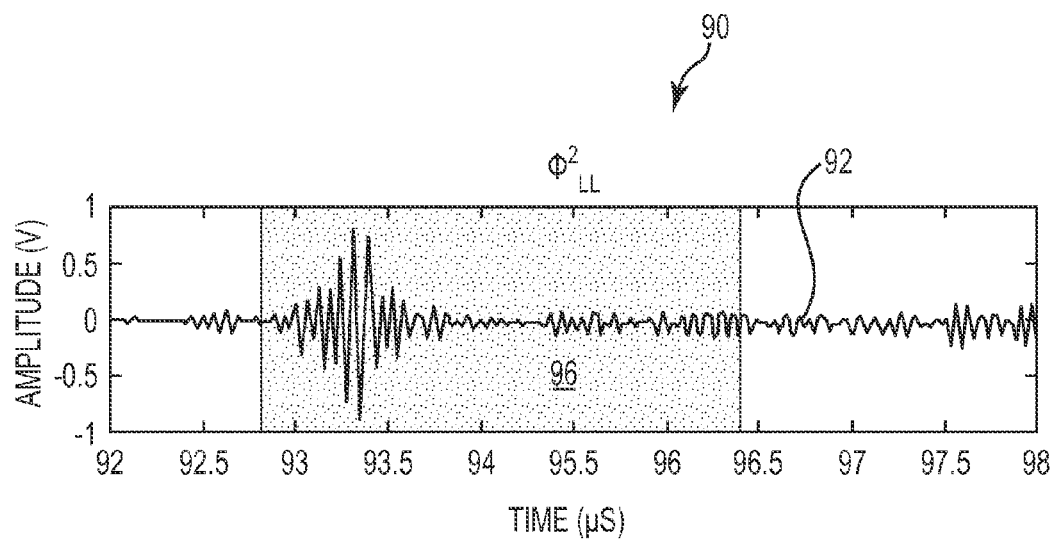
FIG. 7B is a graph showing a sample waveform generated for an oblique incident ultrasonic transducer configuration.

As can be seen in FIGS. 7A-7B, time windows 94, 96 were selected over the approximate single scattering region for performing a statistical analysis on each waveform 88, 92. Time window lengths of $\tau_{TT}$=2.6 µs $\tau_{TT}$=2.6 µs and $\tau_{LL}$=1.3 µs $\tau_{LL}$=1.3 µs is were chosen for the oblique ultrasonic transducer 20, 22 and normal incidence configurations, respectively. By choosing $\tau_{TT}$=2$\tau_{LL}$, the time windows 94, 96 encapsulate, approximately, an equal number of grains in each mode.

Figure 8:
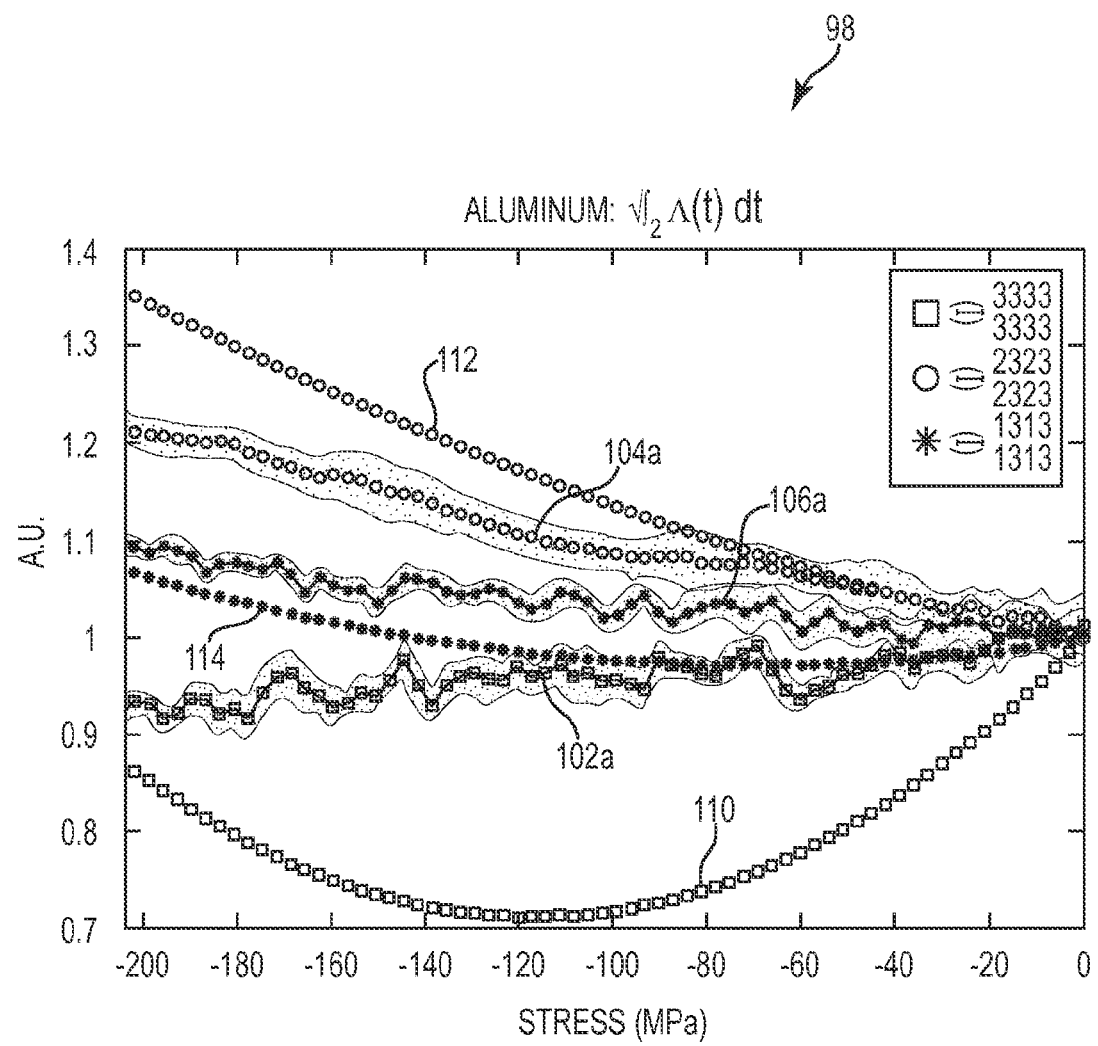
FIG. 8 is a graph showing experimental and theoretical covariance values versus stress for an aluminum specimen.
Figure 9:
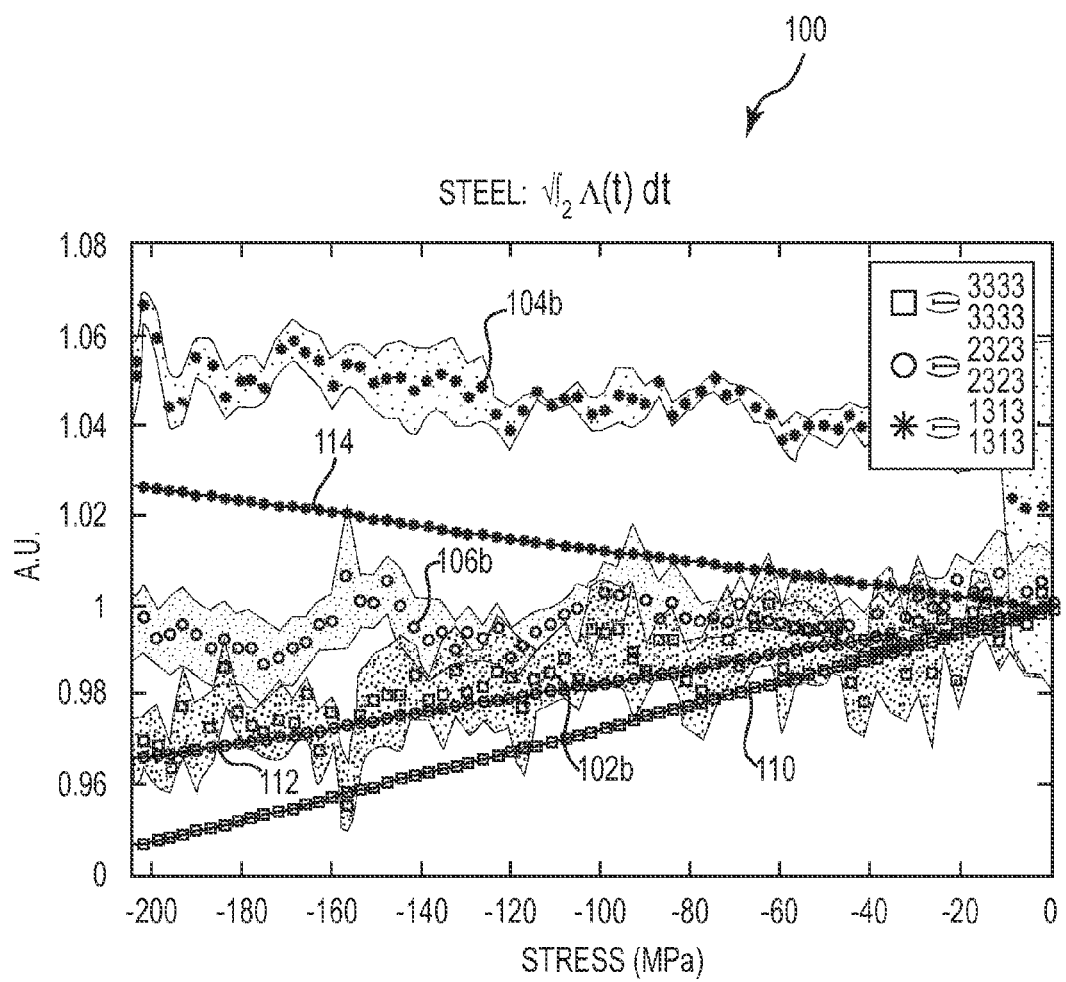
FIG. 9 is a graph showing experimental and theoretical covariance values versus stress for a steel specimen.

By autocorrelating the time-windowed signals, the left-hand side of Equation (6) can then be calculated and compared to the stress dependent elastic covariance tensor. Experimental data were obtained using the method 76 of FIG. 6. Six trials were performed using each transducer orientation. Each trial was averaged and normalized using stress-free values of the sample prior to loading. Theoretical curves were calculated by using Equation (3) with the appropriate coefficients (K) for the steel sample assumed based on coefficients from iron (Fe). FIGS. 8 and 9 are sample graphs 98, 100 showing normalized theoretical stress curves for aluminum and steel obtained by dividing measured stress values by the respective stress-free coefficient, $K_0$. The experimental covariance for the aluminum specimen is represented generally by waveforms 102a, 104a, 106a, with the dashed-line portion of each waveform 102a, 104a, 106a representing the associated standard deviation regions. In similar fashion, the experimental covariance for the steel specimen is represented generally by waveforms 102b, 104b, 106b, with the dashed-line portion of each waveform 102b, 104b, 106b representing the associated standard deviation regions. The theoretical curves 108, 110, 112 for each sample are also shown in FIGS. 8 and 9, using the same respective marker shape.

The transducer orientations conform to the designations shown generally in FIG. 3, in which the longitudinal mode is designated as $\Xi_{1111}^{1111}$ $\Xi_{3333}^{3333}$ and the shear modes are indicated by $\Xi_{2323}^{2323}$ and $\Xi_{1313}^{1313}$. The experimental covariance is sensitive to stress variation. The aluminum sample in FIG. 8 exhibited larger variations than the steel sample in FIG. 9. This behavior was expected since the ratio of $K_2/K_1$ is much larger than for steel. The waveform 104a for aluminum showed a 35% change over the loading range. The standard deviations for the aluminum and steel were on the order of $10^{-3}$. These low standard deviations indicate repeatability of the measurements under multiple loading cycles.

As shown in FIG. 8, the slope of $\Xi_{2323}^{2323}$ is positive whereas the slope of $\Xi_{1313}^{1313}$ is negative. These characteristics may be exploited to predict whether a sample is either under compression or tensile loading. Therefore, shear wave scattering with different polarization directions can be used to predict the type of loading with respect to the loading axis. The difference between the theoretical model and the experimental results may be due in part to not accounting for residual stress or texture information in the theoretical model. The experimental results show similar qualitative characteristics with respect to slope of the effective elastic moduli when compared with the theoretical model.

The second-order statistics of the effective elastic moduli of polycrystals is a function of applied stress. The results from these second-order statistics are thus indicative of scattering behavior that occurs in such materials at ultrasonic frequencies. In contrast to first-order, wavespeed calculations, the second-order statistics (i.e., scattering) for some materials are generally more affected than the first-order statistics (wave speed) with application of load.

Acoustoelasticity refers to the study of the relationship between applied stress and wavespeed within solids. This relationship between stress and wavespeed results from higher-order material behavior that can be neglected when linear-elastic approximations are sufficient for given applications. However, when strains are sufficiently large, the nonlinear behavior is a necessary and important aspect of the component or device response. Acoustoelastic behavior is typically examined in two forms. First, the nonlinear response of single crystals is an important aspect of crystal resonators that undergo large accelerations or applied pressures due to the shifts of the resonant frequencies that typically result. Second, the acoustoelastic response of complex solids is often examined at a macro scale level. Applications involving these materials are typically focused on monitoring stress in materials using ultrasonic methods.

Bridging these two aspects has previously been successful only for polycrystals for which single-crystal nonlinear behavior has been used to predict the nonlinear behavior of an ensemble of randomly oriented crystals. When the influence of applied stress on wavespeeds is the sole interest, the models may rely on only the first-order grain statistics for such predictions. This work has been very successful at connecting the different material scales. In the last several decades, higher-order spatial statistics of polycrystals have been of interest.

The second-order grain statistics, through the covariance of the elastic moduli fluctuations, can be used to connect single crystal properties to ultrasonic scattering behavior that results when high-frequency waves pass through polycrystals. The impedance mismatch due to the misalignment of crystal axes causes energy to be lost from the primary propagation direction due to an energy conserving process. This scattering is most often quantified in terms of the attenuation or diffuse backscatter coefficient.

For unstressed materials, the first-order Voigt-average moduli are often defined as $\langle C_{ijkl}(x)\rangle$, where the angle brackets $\langle\ \rangle$ denote the ensemble average moduli. In many applications, an ergodic hypothesis is assumed such that the ensemble average may be replaced by a spatial average. For the second-order statistics, the quantity of interest, $\langle C_{ijkl}(x) C_{\alpha\beta\gamma\delta}(y)\rangle$, involves two-point statistics. Simplification of this can be made through two assumptions: (1) that the material is spatially homogeneous such that it depends only on the difference between positions x and y, and (2) that the tensorial nature is independent of the spatial nature. Based on these assumptions, the term $\langle C_{ijkl}(x) C_{\alpha\beta\gamma\delta}(y)\rangle$ can be expressed as follows:

$$\langle C_{ijkl} C_{\alpha\beta\gamma\delta}\rangle W(|x-y|); \tag{7}$$

where W is a dimensionless function that contains all spatial dependence.

The average, $\langle C_{ijkl} C_{\alpha\beta\gamma\delta}\rangle$, is dependent on the quantity of the applied stress, and represents an angular average over all possible crystal orientations. For purposes of simplicity, the applied stress on the structure is assumed not to cause any geometric changes to the crystals.

The load-dependent effective elastic moduli $G_{ijkl}$ for a single crystal in terms of the second and third-order elastic moduli can be expressed generally by the following equation:

$$G_{ijkl} = C_{ijkl} + \delta_{ij}\delta_{kP}\delta_{iQ} + 2C_{ijkr}S_{lrPQ} + \\ C_{ijklmn}S_{mnPQ}T_{PQ}G_{ijkl} = C_{ijkl}^I + (\delta_{ij}\delta_{kP}\delta_{iQ} + 2C_{ijkr}S_{lrPQ} + C_{ijklmn}S_{mnPQ}T_{PQ}; \tag{8}$$

where:

$T_{PQ}$ is the applied stress tensor;

$C_{ijklmn}$ is a sixth-rank tensor defining the third order elastic moduli;

$C_{ijkl}$ is a second-order elastic moduli tensor; and $S_{ijkl} = (C_{ijkl})^{-1}$ is a second-order compliance tensor.

For a single crystal with cubic symmetry, the second-order moduli may be written as:

$$C_{ijkl} = C_{ijkl}^I + \delta C_{ijkl} = C_{ijkl}^I + \upsilon \Sigma_{n=1}^3 a_{in}a_{jn}a_{kn}a_{ln}; \tag{9}$$

where $\upsilon = C_{\|} - C_{12} - 2C_{44}$ is the anistropy coefficient for cubic materials.

The isotropic fourth-rank tensor can be given by $C_{ijkl}^I = \lambda^1 \delta_{ij}\delta_{kl} + \mu^1(\delta_{jk}\delta_{il} + \delta_{ik}\delta_{jl}) C_{ijkl}^I = \lambda^1 \delta_{ij}\delta_{kl} + \mu^1(\delta_{ik}\delta_{jl} + \delta_{il}\delta_{jk})$. If the rotation between crystal and laboratory axes is represented by the three Euler angles $\phi, \theta, \zeta$, and the elements of the rotation matrix $a_{ij}$ are given by:

$$a_{ij} = \begin{bmatrix} -\cos\theta\sin\varphi\sin\zeta + \cos\varphi\cos\zeta & \cos\theta\cos\varphi\sin\zeta + \sin\varphi\cos\zeta & \sin\zeta\sin\theta \\ -\cos\theta\sin\varphi\cos\zeta - \cos\varphi\sin\zeta & \cos\varphi\cos\varphi\cos\zeta - \sin\varphi\sin\zeta & \cos\zeta\sin\theta \\ \sin\varphi\sin\theta & -\cos\varphi\sin\theta & \cos\theta \end{bmatrix} \tag{10}$$

Since the angular brackets $\langle\ \rangle$ refer to averages over crystal orientations, the average unstressed moduli can be rewritten as:

$$\langle C_{ijkl}\rangle = C_{ijkl}^I + \upsilon\sum_{n=1}^3 \int a_{in}a_{jn}a_{kn}a_{ln} \frac{\sin\theta d\theta d\varphi d\zeta}{8\pi^2} \langle C_{ijkl}\rangle \\ = C_{ijkl}^I + \upsilon\sum_{n=1}^3 \int a_{in}a_{jn}a_{kn}a_{ln} \frac{\sin\theta d\theta d\varphi d\zeta}{8\pi^2}; \tag{11}$$

where the different combinations of the elements in the rotation matrix in Equation (10) above are integrated over the unit sphere.

To consider the effective moduli for materials with cubic symmetric under an applied stress, the following third-order elastic modulus tensor can be used:

$$C_{ijklmn} = C_{123}\delta_{ijklmn}^1 + C_{144}\delta_{ijklmn}^2 + C_{456}\delta_{ijklmn}^3 + \\ d_1 A_{ijklmn}^1 d_2 A_{ijklmn}^2 + d_3 A_{ijklmn}^3; \tag{12}$$

where $d_1$, $d_2$ and $d_3$ are three anisotropic constants defined using the six independent third-order elastic constants as $d_1 = C_{111} - 3C_{112} + 2C_{123} + 12C_{144} - 12C_{166} + 16C_{456}$, $d2 = C_{112} - C_{123} - 2C_{144}$ and $d3 = C_{166} - C_{144} - 2C_{456}$. The isotropic base tensors $\delta^1$, $\delta^2$, and $\delta^3$ in Equation (12) can be determined based on the following functions:

$$\delta_{ijklmn}^1 = \delta_{ij}\delta_{kl}\delta_{mn}$$

$$\delta_{ijklmn}^2 = 2(\delta_{ij}I_{klmn} + \delta_{kl}I_{ijmn} + \delta_{mn}I_{ijkl})$$

-continued $$\delta^3_{ijklmn} = 2(\delta_{ik}I_{jlmn} + \delta_{il}I_{jkmn} + \delta_{im}I_{jnkll} + \delta_{in}I_{jmkl})$$

$$I_{ijkl} = \frac{1}{2}(\delta_{ik}\delta_{jl} + \delta_{il}\delta_{jk})$$

The base tensors $A^1$, $A^2$ and $A^3$ in Equation (12) can be written in terms of the components of the rotation matrix as follows:

$$A_{ijklmn}^{1} = a_{iu}a_{ju}a_{ku}a_{lu}a_{mu}a_{nu}, A_{ijklmn}^{2} = \delta_{ij}a_{ku}a_{lu}a_{mu}a_{nu} + \delta_{kl}a_{iu}a_{ju}a_{mu}a_{nu} + \delta_{mn}a_{iu}a_{ju}a_{ku}a_{lu}, A_{ijklmn}^{3} = \delta_{ik}a_{ju}a_{lu}a_{mu}a_{nu} + \delta_{il}a_{ku}a_{ju}a_{mu}a_{nu} + \delta_{jm}a_{iu}a_{ku}a_{lu}a_{nu} + \delta_{jn}a_{iu}a_{ku}a_{lu}a_{mu} + \delta_{jk}a_{iu}a_{ju}a_{ku}a_{lu} + \delta_{jl}a_{iu}a_{ku}a_{mu}a_{nu} + \delta_{jm}a_{iu}a_{ku}a_{lu}a_{nu} + \delta_{jn}a_{iu}a_{ku}a_{lu}a_{mu} + \delta_{km}a_{iu}a_{ju}a_{lu}a_{nu} + \delta_{kn}a_{iu}a_{ju}a_{lu}a_{mu} + \delta_{lm}a_{iu}a_{ju}a_{ku}a_{nu} + \delta_{ln}a_{iu}a_{ju}a_{ku}a_{mu}$$

The mean of the effective elastic modulus tensor can thus be written as:

$$<G_{ijkl}> = <C_{ijkl}> + \delta_{jl}\delta_{kP}\delta_{lQ}T_{PQ} + 2<C_{ijkr}S_{lrPQ}>T_{PQ} + <C_{ijklmn}S_{mnPQ}>T_{PQ}. \quad (13)$$

The covariance of the effective (stress-dependent) elastic moduli may be expressed in a format similar to Equation (13) above.

Combining Equations (7) through (12) above yields the following simplified equation for determining the covariance:

$$\Xi_{ijkl}^{\alpha\beta\gamma\delta} = G_{ijkl}G_{\alpha\beta\gamma\delta} - \\
<G_{ijkl}><G_{\alpha\beta\gamma\delta}> = <C_{ijkl}C_{\alpha\beta\gamma\delta}> - \\
<C_{ijkl}><C_{\alpha\beta\gamma\delta}> + (2(<C_{ijkr}S_{lrPQ}C_{\alpha\beta\gamma\delta}> - \\
<C_{ijkr}S_{lrPQ}><C_{\alpha\beta\gamma\delta}>) + <C_{ijklmn}S_{mnPQ}C_{\alpha\beta\gamma\delta}> - \\
<C_{ijklmn}S_{mnPQ}><C_{\alpha\beta\gamma\delta}>)T_{PQ} + \\
(<C_{ijkl}C_{\alpha\beta\gamma\delta\sigma\lambda}S_{\sigma\lambda RT}> - <C_{ijkl}><C_{\alpha\beta\gamma\delta\sigma\lambda}S_{\sigma\lambda RT}> + \\
2(<C_{ijkl}C_{\alpha\beta\gamma p}S_{\delta\rho RT}> - <C_{ijkl}><C_{\alpha\beta\gamma p}S_{\delta\rho RT}>))\\
T_{RT} + 4(<C_{ijkr}S_{lrPQ}C_{\alpha\beta\gamma\delta}S_{\delta\rho RT}> - \\
<C_{ijkr}S_{lrPQ}><C_{\alpha\beta\gamma p}S_{\delta\rho RT}>)T_{RT}T_{PQ} + 2\\
(<C_{ijklmn}S_{mnPQ}C_{\alpha\beta\gamma p}S_{\delta\rho RT}> - \\
<C_{ijklmn}S_{mnPQ}><C_{\alpha\beta\gamma p}S_{\delta\rho RT}>)T_{RT}T_{PQ} + 2\\
(<C_{ijkr}S_{lrPQ}C_{\alpha\beta\gamma\delta\sigma\lambda}S_{\sigma\lambda RT}> - \\
<C_{ijkr}S_{lrPQ}><C_{\alpha\beta\gamma\delta\sigma\lambda}S_{\sigma\lambda RT}>)T_{RT}T_{PQ} + \\
(<C_{ijklmn}S_{mnPQ}C_{\alpha\beta\gamma\delta\sigma\lambda}S_{\sigma\lambda RT}> - \\
<C_{ijklmn}S_{mnPQ}><C_{\alpha\beta\gamma\delta\sigma\lambda}S_{\sigma\lambda RT}>)T_{RT}T_{PQ}. \quad (14)$$

As can be seen from Equation (14) above, the necessary components of the covariance can thus be found in terms of the second-order modulus and compliance tensors and the third-order modulus tensor.

To determine the covariance computationally, only nine terms are needed due to the symmetry of the several terms. The covariance varies quadratically with applied stress, and can thus be expressed in condensed form in terms of the magnitude of the applied stress as follows:

$$\Xi_{ijkl}^{\alpha\beta\gamma\delta}(T) = K_0 K_1 T + K_2 T^2, \quad (15)$$

where $K_0$, $K_1$, and $K_2$ are load independent constants related to the directionality of the applied stress as well as the components $ijkl$ and $\alpha\beta\gamma\delta$ (which implicitly depend from the load independent constants). The coefficient $K_0$ is the covariance of the elastic moduli for the unstressed material. Coefficients $K_1$ and $K_2$, in turn, are stress-dependent components.

For uniaxial loading, the material can be assumed to be loaded along the I-direction such that the four subscripts in Equation (14) are given as R=T=P=Q=1. For purposes of analysis, the determination can be limited to four specific cases. The quantities, $\Xi_{2222}^{2222} = \Xi_{3333}^{3333}$, are related to normal incidence ultrasonic backscatter in a direction perpendicular to the applied uniaxial load while $\Xi_{1111}^{1111}$ is related to ultrasonic backscatter in the direction parallel to the applied load. Finally, two other components, $\Xi_{1313}^{1313}$ and $\Xi_{2323}^{2323}$, are examined since these are associated with shear wave scattering.

The second-order and third-order elastic constants for several important materials with cubic symmetry are known in the art. The numerical values of $K_0$, $K_1$, and $K_2$ are also known in the art for these materials. For certain types of materials and applies stresses, the values of $K_2$ are typically positive such that scattering generally increases with applied stress that is either tensile or compressive. In addition, the sign of $K_1$ may be positive or negative depending on the material and mode type. Thus, the minimum of $\Xi$ may occur in either compression or tension at a value of applied stress, where $T_{min} = -K_1/(2K_2)$. Furthermore, the relative change in $\Xi$ for each material $(K_2/K_0)$ shows the overall degree of acoustoelastic response that can be expected in the scattered behavior.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for ultrasonically determining one or more microstructural material properties of a structural specimen, comprising:
   a. transmitting a plurality of pulsed ultrasonic waves to a single point on a structural specimen;
   b. sensing ultrasonic backscatter signals responsive to the pulsed ultrasonic waves;
   c. selecting a time window for analyzing the ultrasonic backscatter signals; performing an autocorrelation function on the time-windowed ultrasonic backscatter signals wherein the autocorrelation function comprises an autocorrelation algorithm configured to analyze a single scattering response model further comprising a second-order elastic modulus and compliance tensor and a third-order elastic modulus; and
   d. determining one or more microstructural material properties of the structural specimen.

2. The method of claim 1, further comprising:
   a. a plurality of ultrasonic transducers configured for operating in a pulse-echo mode for transmitting ultrasonic waves to a target region on or within a structural specimen and receiving ultrasonic backscatter signals responsive to the ultrasonic waves; and
   b. an evolution module configured for receiving the ultrasonic backscatter signals, the evolution module configured for performing a statistical autocorrelation function on the ultrasonic backscatter signals and determining one or more microstructural material properties of the specimen.

3. The method of claim 2, wherein the plurality of ultrasonic transducers comprises:
   a. a normal incidence ultrasonic transducer configured to transmit ultrasonic waves at an angle normal to the structural specimen for inducing a longitudinal wave mode in the specimen; and
   b. a plurality of oblique incidence ultrasonic transducers each configured to transmit ultrasonic waves at an angle oblique to the structural specimen for inducing a shear wave mode in the specimen.

4. The method of claim 3, wherein the plurality of oblique incidence ultrasonic transducers comprises a first oblique incidence ultrasonic transducer and a second oblique incidence ultrasonic transducer.

5. The method of claim 4, wherein the first oblique incidence ultrasonic transducer is located at a first oblique angle to the structural specimen, and wherein the second oblique incidence ultrasonic transducer is located at a second oblique angle to the structural specimen different than the first oblique angle.

6. The method of claim 2, wherein the evaluation module comprises a controller configured to execute an autocorrelation algorithm for evaluating the ultrasonic backscatter signals.

7. The method of claim 6, wherein the autocorrelation algorithm comprises a single scattering response model.

8. The method of claim 7, wherein the single scattering response model comprises second order grain statistics of the structural specimen.

9. The method of claim 2, wherein the evaluation module comprises a means for acquiring and associating global location data with a location of the target region.

10. The method of claim 2, wherein the evaluation module comprises a means for wirelessly relaying ultrasonic backscatter data to a remote device.

11. The method of claim 2, wherein the target region comprises a single point on the structural specimen.

12. A method for ultrasonically determining one or more microstructural material properties of a structural specimen, comprising:
   a. transmitting a plurality of pulsed ultrasonic waves to a single point on a structural specimen;
   b. sensing ultrasonic backscatter signals responsive to the pulsed ultrasonic waves;
   c. selecting a time window for analyzing the ultrasonic backscatter signals;
   d. performing an autocorrelation function on the time-windowed ultrasonic backscatter signals, wherein performing an autocorrelation function on the time-windowed ultrasonic backscatter signals further comprises:
      i. computing an autocorrelation function for each of a plurality of data points of the backscatter signals;
      ii. computing a mean autocorrelation value;
      iii. integrating the computed autocorrelation function for each data point and the mean autocorrelation value over the time window to obtain an integrated value; and
      iv. comparing the root of the integrated value to a variance integral over the time window; and
   e. determining one or more microstructural material properties of the structural specimen.

13. The method of claim 12, further comprising:
   a. a plurality of ultrasonic transducers configured for operating in a pulse-echo mode for transmitting ultrasonic waves to a target region on or within a structural specimen and receiving ultrasonic backscatter signals responsive to the ultrasonic waves; and
   b. an evolution module configured for receiving the ultrasonic backscatter signals, the evolution module configured for performing a statistical autocorrelation function on the ultrasonic backscatter signals and determining one or more microstructural material properties of the specimen.

14. The method of claim 13, wherein the plurality of ultrasonic transducers comprises:
   a. a normal incidence ultrasonic transducer configured to transmit ultrasonic waves at an angle normal to the structural specimen for inducing a longitudinal wave mode in the specimen; and
   b. a plurality of oblique incidence ultrasonic transducers each configured to transmit ultrasonic waves at an angle oblique to the structural specimen for inducing a shear wave mode in the specimen.

15. The method of claim 14, wherein the plurality of oblique incidence ultrasonic transducers comprises a first oblique incidence ultrasonic transducer and a second oblique incidence ultrasonic transducer.

16. The method of claim 15, wherein the first oblique incidence ultrasonic transducer is located at a first oblique angle to the structural specimen, and wherein the second oblique incidence ultrasonic transducer is located at a second oblique angle to the structural specimen different than the first oblique angle.

17. The method of claim 13, wherein the evaluation module comprises a controller configured to execute an autocorrelation algorithm for evaluating the ultrasonic backscatter signals.

18. The method of claim 17, wherein the autocorrelation algorithm comprises a single scattering response model.

19. The method of claim 18, wherein the single scattering response model comprises second order grain statistics of the structural specimen.

20. The method of claim 13, wherein the evaluation module comprises a means for acquiring and associating global location data with a location of the target region.

21. The method of claim 13, wherein the evaluation module comprises a means for wirelessly relaying ultrasonic backscatter data to a remote device.

22. The method of claim 13, wherein the target region comprises a single point on the structural specimen.

* * * * *

UNITED STATES PATENT AND TRADEMARK OFFICE
CERTIFICATE OF CORRECTION

PATENT NO. : 8,857,262 B2
APPLICATION NO. : 13/305888
DATED : October 14, 2014
INVENTOR(S) : Turner et al.

It is certified that error appears in the above-identified patent and that said Letters Patent is hereby corrected as shown below:

In the Claims:

Claim 2, column 14, on lines 46 and 47, "evolution" should be -evaluation-

Claim 13, column 16, on lines 3 and 4, "evolution" should be -evaluation-

Signed and Sealed this
Second Day of June, 2015

Michelle K. Lee
*Director of the United States Patent and Trademark Office*